United States Patent
Schwarz

(10) Patent No.: US 9,951,110 B2
(45) Date of Patent: Apr. 24, 2018

(54) NEUROPEPTIDES USEFUL AS INSECTICIDES

(71) Applicant: THE STATE OF ISRAEL, MINISTRY OF AGRICULTURE & RURAL DEVELOPMENT, AGRICULTURAL RESEARCH ORGANIZATION (ARO), (VOLCANI CENTER), Bet Dagan (IL)

(72) Inventor: Miriam Altstein Schwarz, Rehovot (IL)

(73) Assignee: The State of Israel Agriculture Research Org, Bet Dagan (IL)

( * ) Notice: Subject to any disclaimer, the term of this patent is extended or adjusted under 35 U.S.C. 154(b) by 0 days.

(21) Appl. No.: 15/027,822

(22) PCT Filed: Sep. 21, 2014

(86) PCT No.: PCT/IL2014/050841
§ 371 (c)(1),
(2) Date: Apr. 7, 2016

(87) PCT Pub. No.: WO2015/052701
PCT Pub. Date: Apr. 16, 2015

(65) Prior Publication Data
US 2016/0355556 A1 Dec. 8, 2016

(30) Foreign Application Priority Data

Oct. 7, 2013 (IL) .......................... 228768

(51) Int. Cl.
*C07K 14/435* (2006.01)
*A01N 37/46* (2006.01)
*A01N 63/00* (2006.01)

(52) U.S. Cl.
CPC ........ *C07K 14/43563* (2013.01); *A01N 37/46* (2013.01); *A01N 63/00* (2013.01)

(58) Field of Classification Search
None
See application file for complete search history.

(56) References Cited

U.S. PATENT DOCUMENTS 5,032,576 A 7/1991 Raina et al.

FOREIGN PATENT DOCUMENTS

JP 4-208300 A 7/1992
WO WO 95/29191 A1 11/1995

OTHER PUBLICATIONS

Zelster et al., "Discovery of a linear lead antagonist to the insect pheromone biosynthesis activating neuropeptide (PBAN)", Peptides, 2000, 1457-1465.*
Zhang et al., "Disruption of insect diapause using agonists and an antagonist of diapause hormone", PNAS, 2011, pp. 16922-16926.*
Adessi et al., "Converting a Peptide into a Drug: Strategies to Improve Stability and Bioavailability", Current Medicinal Chemistry, 2002, pp. 963-978.*
Ben-Aziz et al., "PBAN selective antagonists: inhibition of PBAN induced cuticular melanization and sex pheromone biosynthesis in moths", Journal of Insert Physiology, 2005, 305-314.*
Alstein, M., et al., "Inhibition of PK/PBAN-mediated functions in insects: Discovery of selection and non-selective inhibitors," Peptides, vol. 28, pp. 574-584, 2007.
Hariton, A., et al., "Bioavailability of β-amino acid and C-terminally derived PK/PBAN analogs," Peptides, vol. 30, pp. 2174-2181, 2009.
Nachman, R.J., et al., "An amphiphilic, PK/PBAN analog is a selective pheromonotropic antagonist that penetrates the cuticle of a heliothine insect," Peptides, vol. 30, pp. 616-621, 2009.
Patent Cooperation Treaty, International Search Report, International Patent Application No. PCT/IL2014/050841, dated Dec. 17, 2014, 4 Pages.
Patent Cooperation Treaty, Written Opinion of the International Searching Authority, International Patent Application No. PCT/IL2014/050841, dated Dec. 17, 2014, 7 Pages.
European Extended Search Report, European Application No. 14852937.3, dated Feb. 17, 2017, 9 pages.
Zeltser, I. et al., "Discovery of a Linear Lead Antagonist to the Insect Pheromone Biosynthesis Activating Neuropeptide (PBAN)". Peptides, 2000, pp. 1457-1465, vol. 1, No. 10, XP 055342421.

* cited by examiner

*Primary Examiner* — Lianko G Garyu
(74) *Attorney, Agent, or Firm* — Fenwick & West LLP

(57) ABSTRACT

The invention provides short peptides derived from an insect neuropeptide for controlling insects, particularly peptides or their analogs derived from PBAN family neuropeptide having at least one dPhe residue. The invention further provides an environmentally friendly method for controlling and/or preventing insect infestation by applying the short peptides in very low concentrations.

6 Claims, 14 Drawing Sheets

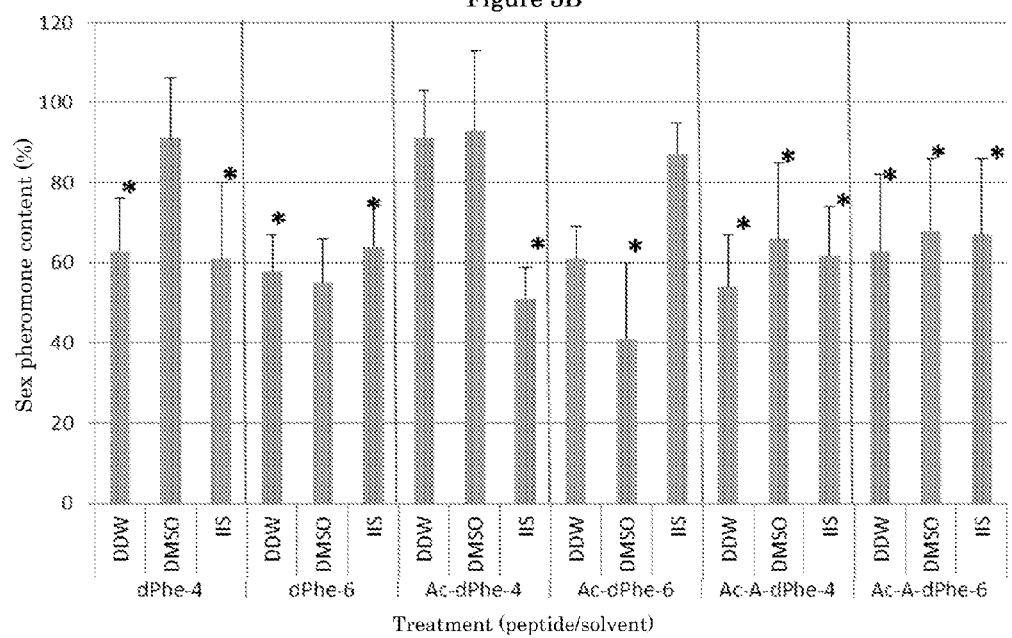

NEUROPEPTIDES USEFUL AS INSECTICIDES

RELATED APPLICATIONS

This application is a 35 U.S.C. 371 national stage filing of International Application No. PCT/IL2014/050841, filed on Sep. 21, 2014, which claims priority from Israel Patent Application No. 228768 filed on Oct. 7, 2013. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Aug. 8, 2016, is named 33601US_CRF_sequencelisting.txt and is 7,780 bytes in size.

FIELD OF THE INVENTION

The present invention relates to peptide fragments and analogs derived from the amino acid sequence of pyrokinin (PK)/pheromone biosynthesis activating neuropeptide PBAN family, having inhibitory biological activities in insects. The peptide fragments of the invention are useful insecticides as they, e.g., disrupt pheromone production, melanization and other PK/PBAN controlled activities.

The present invention also relates to a method for controlling insects by applying the abovementioned peptide fragments to the insects, either by topical application, e.g. by spraying the environment, the plants or the insects themselves, or by feeding or watering the insects with food-stuff or water containing said peptide fragments.

BACKGROUND OF THE INVENTION

Neuropeptides play a key role in the regulation of a variety of physiological functions in insects. For example, they are involved in embryonic and post-embryonic development (e.g. molting, diapause and metamorphosis), in homeostasis, osmoregulation, diuresis and digestion. Insect neuropeptides are also known to control essential behavioral patterns such as migration, mating and oviposition.

Insect neuropeptides are involved in a variety of physiological processes, and therefore have great potential as pest control agents, based on the interference with their activity. The present invention addresses one step in the course of the neuroendocrine regulation, namely, binding of the neuropeptides to their receptors and activation of their target organ. Specifically, the present invention deals with the inhibitory activity of peptide fragments derived from the PK/PBAN family of peptides.

Sexual communication between male and female moths is regulated by sex pheromones. Sex pheromones are synthesized and secreted by the female from the pheromone gland. The inability of the female to produce sex pheromones results in a marked decrease in mating and thus, significantly reduces the insect population. Due to their important role in mating, sex pheromones have been studied intensively. For instance, it has been found that moths sex pheromones consist of blends of $C_{10}$-$C_{18}$ aliphatic compounds. The diversity between pheromones of different species is indicated by differences in the chain length, the position and configuration of the olefinic bonds, and by the chemical nature of the functional group. Most pheromones are aldehydes, alcohols or acetates. Some, however, may appear as epoxides, ketones and hydrocarbons.

It has been found that a neuroendocrine factor, termed PBAN, is involved in the regulation of sex pheromone biosynthesis. PBAN is a linear C-terminally amidated peptide containing 33 amino acids. PBAN's structure has been fully identified, and since 1989, its primary amino acid sequences has been revealed in over twenty moth species. PBAN is synthesized in the brain and subesophageal ganglion that projects to the corpora cardiaca, and in ganglia of the ventral nerve cord. The peptide is either transported to its target organ via the hemolymph or acts locally. It is present in both male and female moth and its biological activity is mediated by cAMP and depends on the presence of $Ca^{-+}$ ions.

Further studies of insect neuropeptides revealed that the C-terminal sequence of PBAN—(X=S) FXPRLa (SEQ ID NO: 1)—is also present in other insect neuropeptides (where X represents S, T, G or V). All peptides sharing the above sequences were grouped into one family, which was designated as the FXPRLa family or the PK/PBAN family. In addition to the pheromonotropic activity of this family, PK/PBAN peptides and fragments derived therefrom, have also been shown to control cuticular melanization, muscle contraction and embryonic and pupal diapause.

JP 4-208300 describes the full 33 amino acid sequence of the PBAN peptide isolated from silkworms, as well as some of its fragments.

U.S. Pat. No. 5,032,576 relates to the isolation, characterization and synthesis of PBAN from Helicoverpa zea. U.S. Pat. No. 5,032,576 uses the full length PBAN and several analogs thereof (all of which are 33 amino acid long) for controlling female moths or larvae. However, U.S. Pat. No. 5,032,576 does not suggest or even hints towards the possibility of using shorter PBAN fragments.

One way to inhibit PK/PBAN peptides is by antagonists, which are selective inhibitors capable of blocking the receptor site of the neuropeptide, and thus, preventing from the endogenous peptide to bind to the receptor and exert their biological activity. Therefore, PK/PBAN antagonists can serve as specific inhibitors for their activity, and may serve as potential insecticides.

A substantial problem/challenge in the implementation of the above strategy for insect management is that there are no defined protocols to convert peptide agonists into antagonists. In addition, neuropeptides are unstable and readily attacked by enzymes. Therefore, developing neuropeptides as antagonistic compounds is not common. One way to overcome the problem is based on searching and creating peptidomimetic compounds which show enhanced biological stability. In order to design peptidomimetic antagonists, the structure-activity relationship of the peptides has to be revealed, conformationally constrained analogs based on their active site have to be designed and synthesized, then the active and inactive residues in those molecules have to be identified and peptidomimetic compounds containing the active residues have to be designed, synthesized and tested for stable antagonistic activity. This is usually a highly laborious and long process based on availability of many peptide libraries as well as a detailed instrumental chemical analysis combined with highly advanced in silico computational analysis. The entire operations requires expertise in peptide chemistry and instrumental analytical chemistry, without any promise or means to predict success. Once completed, such an approach leads to the discovery of many peptidomimetic compounds, most of which are very expensive in production and are also found, in many cases, to be ineffective.

Accordingly, one object of the invention is to simplify the process and to provide novel peptide-based antagonists which show high inhibitory potency and high stability and bioavailability on one hand, and which are simple to design and synthesize on the other. In addition, another object is to make said production cost-effective. Said antagonists are 5 to 6 amino acids long, and are derived from the PK/PBAN sequence.

In order to be effective, insecticides should be able to penetrate the insect's cuticle and/or be stable upon ingestion. Therefore, it is preferred to use insecticides with a low molecular weight. Accordingly, one embodiment of the invention are low molecular weight peptides which demonstrate high cuticle-penetration capabilities as well as stability upon ingestion. In another embodiment, the present invention relates to peptides which include a supplementary residue which further increases their cuticle- and oral penetration capabilities.

SUMMARY OF THE INVENTION

The present invention provides peptide-fragments derived from the amino acid sequence of pyrokinin/pheromone biosynthesis activating neuropeptide (PK/PBAN) showing inhibitory biological activity at low doses (1-100 pmol), and their use as insecticides. These PK/PBAN derived peptides of the invention can act in different ways, e.g., by disrupting pheromone production, melanization and other activities controlled by the PK/PBAN peptide family.

The PK/PBAN peptide-fragments of the invention may have the formula:

X-Arg-Tyr-Phe-Y-Leu-amide (SEQ ID NO: 2) or (ii)
    X-Ala-Y-Leu-amide                               (SEQ ID NO: 3)

wherein X is Acetyl, Fmoc, or Cyclohexyl, and Y is [dPhe]-Pro-Arg or Ser-Pro-[dPhe].

According to one embodiment, the PK/PBAN peptide-fragments of the invention are selected from the group consisting of: Acetyl-Arg-Tyr-Phe-[dPhe]-Pro-Arg-Leu-amide (SEQ ID NO: 4); and Acetyl-Arg-Tyr-Phe-Ser-Pro-[dPhe]-Leu-amide (SEQ ID NO: 5).

According to another embodiment, the PK/PBAN peptide-fragments of the invention are selected from the group consisting of: Acetyl-Ala-[dPhe]-Pro-Arg-Leu-amide (SEQ ID NO: 6); Acetyl-Ala-Ser-Pro-[dPhe]-Leu-amide (SEQ ID NO: 7); Cyclohexyl-Ala-[dPhe]-Pro-Arg-Leu-amide (SEQ ID NO: 8); Cyclohexyl-Ala-Ser-Pro-[dPhe]-Leu-amide (SEQ ID NO: 9); Fmoc-Ala-[dPhe]-Pro-Arg-Leu-amide (SEQ ID NO: 10); and Fmoc-Ala-Ser-Pro-[dPhe]-Leu-amide (SEQ ID NO: 11).

The present invention also provides the above mentioned PK/PBAN peptide-fragments for use as insecticides or as insect control agents. In addition, the invention provides the use of said PK/PBAN peptide-fragments in the preparation of insecticides or insect control agents.

Also disclosed herein are compositions for controlling insects comprising peptide fragments and/or analogs derived from the amino acid sequence of PK/PBAN, having at least one dPhe residue, wherein said peptide fragments and/or analogs have improved cuticle penetrability and/or oral bioavailability and/or environmental stability.

According to one embodiment, said composition is an insecticide composition comprising the PK/PBAN peptide-fragments of the invention. According to another embodiment, said composition is an insect control composition comprising the PK/PBAN peptide-fragments of the invention.

The present invention also provides a method for controlling and/or preventing insect infestation comprising dispersing at least one of the PK/PBAN peptide-fragments of the invention, or the composition of the invention, and an agricultural acceptable carrier onto the desired area.

According to one aspect, the method for controlling and/or preventing insect infestation according to the invention, comprises administering at least one of the above mentioned PK/PBAN peptide-fragments, or compositions, to the insects by applying them to agricultural products or a desired area. Alternatively, said method is carried out by feeding the insects with said compounds or compositions.

The present invention also provides the use of at least one of the above mentioned PK/PBAN peptide-fragments, or compositions comprising them, in conjunction with a solvent, and optionally another insecticide, in the preparation of an insecticide or an insect control composition. According to one aspect, said solvent is IIS (which consists of 0.5% ethanol, 0.05% Tween-80 in DDW), DMSO or DDW (double-distilled water).

The above and other objects and advantages of invention will become apparent as the description proceeds.

Unless otherwise stated, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In addition, the materials, methods, and examples are illustrative only and are not intended to be necessarily limiting.

BRIEF DESCRIPTION OF THE DRAWINGS

The above and other characteristics and advantages of the invention will be more readily apparent through the following examples, and with reference to the appended drawings, wherein.

Agonistic activity is expressed as a percentage of the degree of melanization obtained with 5 pmol PBAN (defined as 100%). Statistical analysis compared activity of each peptide with that obtained with 5 pmol PBAN.

The tested peptides are those listed in Table 1 (1-10, respectively).

Figure 2:
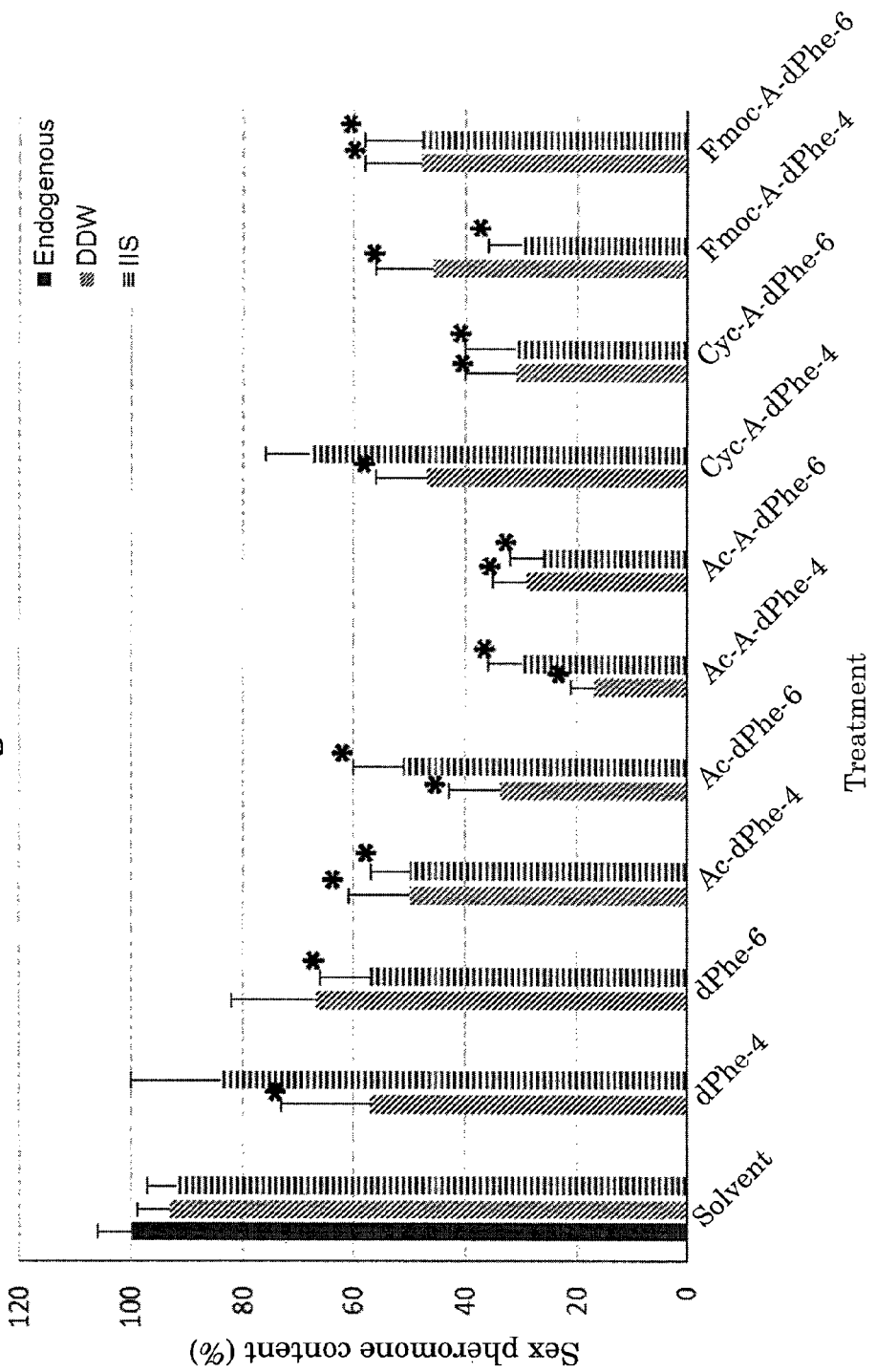

FIG. 2. is a graph showing the effect of topically applied peptides on the inhibition of sex pheromone biosynthesis in *Heliothis peltigera* female moths.

The tested peptides are those listed in Table 1 (1-10, respectively).

Peptides were tested at a concentration of 10 pmol and were applied in IIS (0.5% ethanol, 0.05% Tween-80 in DDW), and DDW for 1 h.

Sex pheromone content is expressed as a percentage of the endogenous pheromone content obtained using control untreated moths (defined as 100%). Statistical analysis compared pheromone content in the presence of each peptide with that obtained with the corresponding solvents themselves (indicated by an asterisk).

There was no significant difference between the amount of pheromone content generated by untreated control females and that of the solvent (DDW or IIS) treated moths.

Figure 3A:
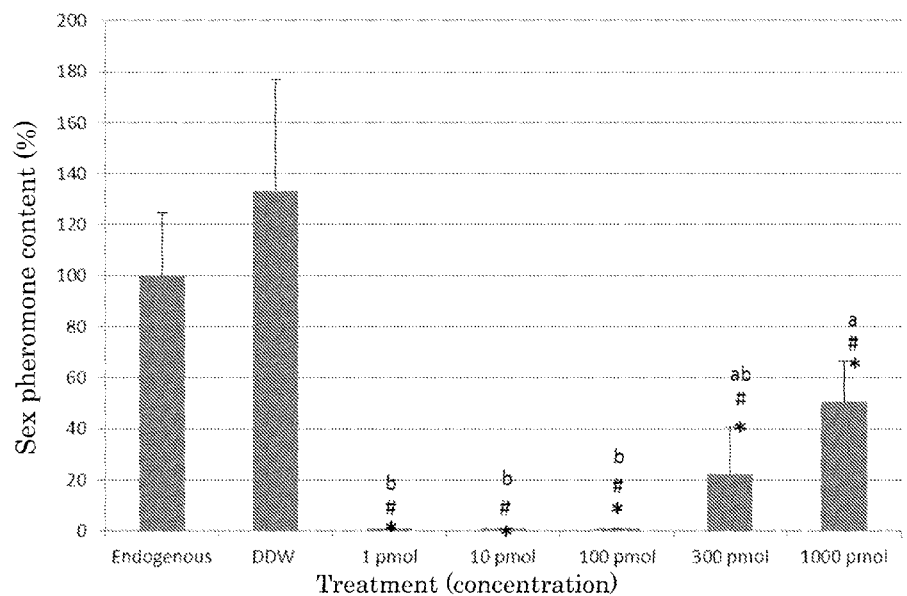
Figure 3B:
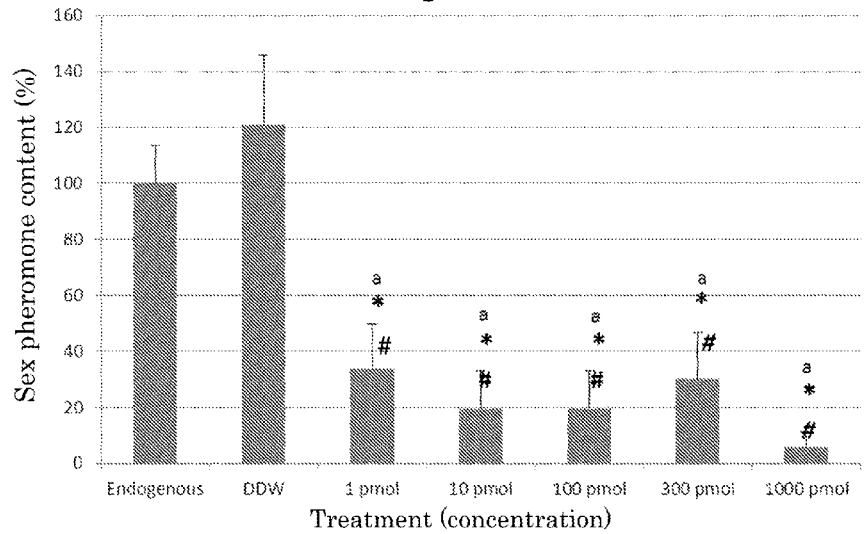

FIG. 3A and FIG. 3B are graphs showing the dose response of Ac-A-dPhe-4 (3A) or Ac-A-dPhe-6 (3B) on inhibition of sex pheromone biosynthesis in *Heliothis peltigera* female moths. Peptides were applied in DDW for 1 h.

Sex pheromone content is expressed as a percentage of the endogenous pheromone content obtained using control untreated moths (defined as 100%). Statistical analysis compared pheromone content in the presence of each peptide at the indicated concentrations with that obtained with the solvent itself (indicated by an asterisk). A similar statistical analysis was also made against the pheromone content of untreated moths (indicated by #). There was no significant difference between the amount of pheromone content generated by untreated control females and that of the solvent (DDW) treated moths. Differences in the potency of the peptides at the indicated concentrations are depicted by letters. Bars with the same letter do not differ significantly.

Figure 4:
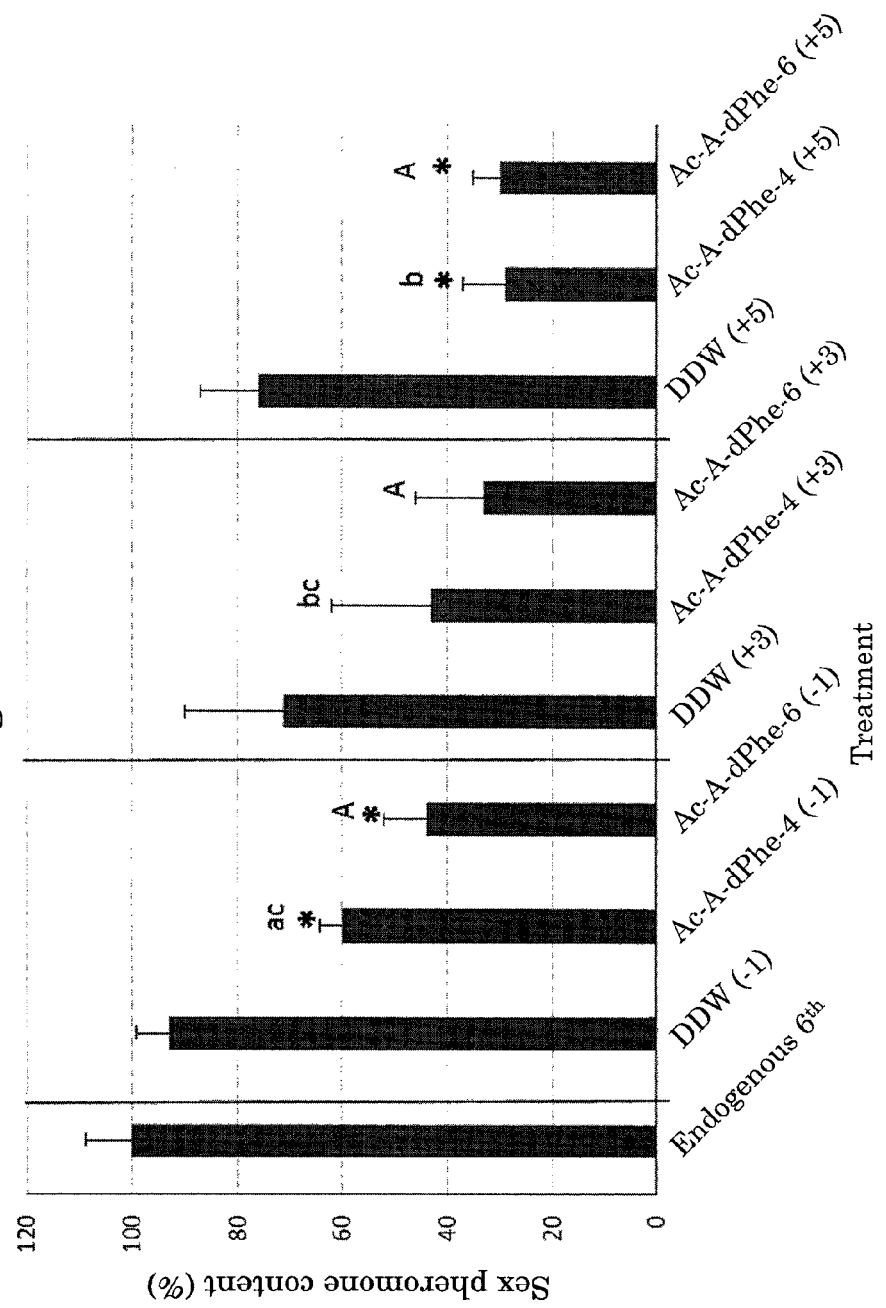

FIG. 4. is a graph showing the time response of 1 nmol Ac-A-dPhe-4 and Ac-A-dPhe-6 (applied in DDW) on inhibition of sex pheromone biosynthesis in *Heliothis peltigera* female moths.

Sex pheromone content is expressed as a percentage of the endogenous pheromone content obtained using control untreated moths (defined as 100%). Statistical analysis compared pheromone content in the presence of each peptide at the indicated times with that obtained with the solvent itself at the same time point (indicated by an asterisk). There was no significant difference between the amount of pheromone content generated by untreated control females and that of the solvent (DDW) treated moths at the indicated time points. Differences in the potency of the peptides at the indicated time points are depicted by letters. (Ac-A-dPhe-4: small letters; Ac-A-dPhe-6: capital letters). Bars with the same letter do not differ significantly.

Figure 5A:
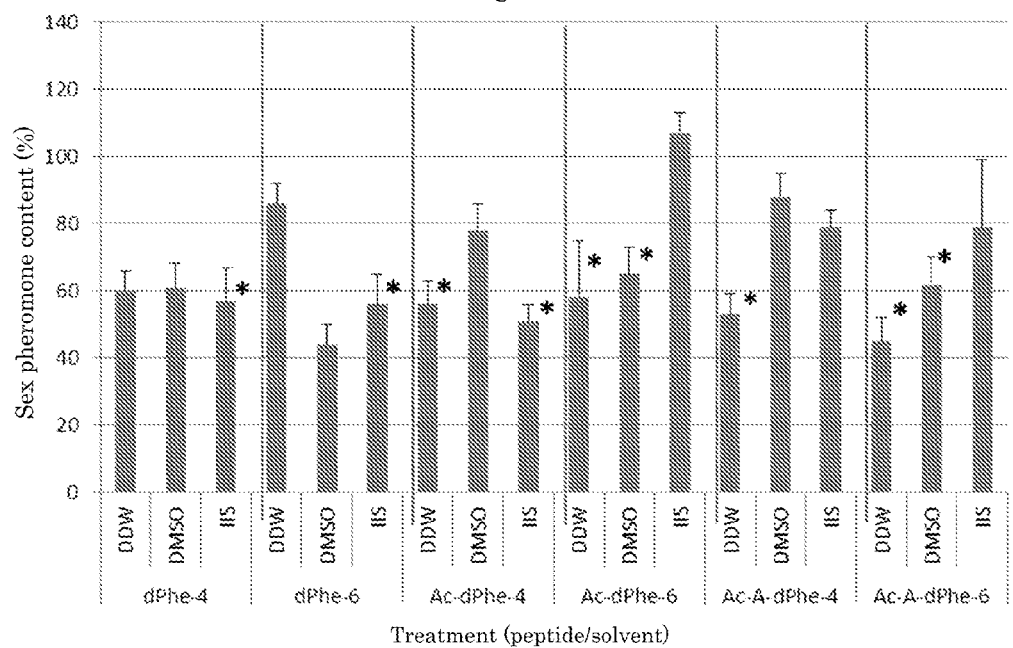
Figure 5C:
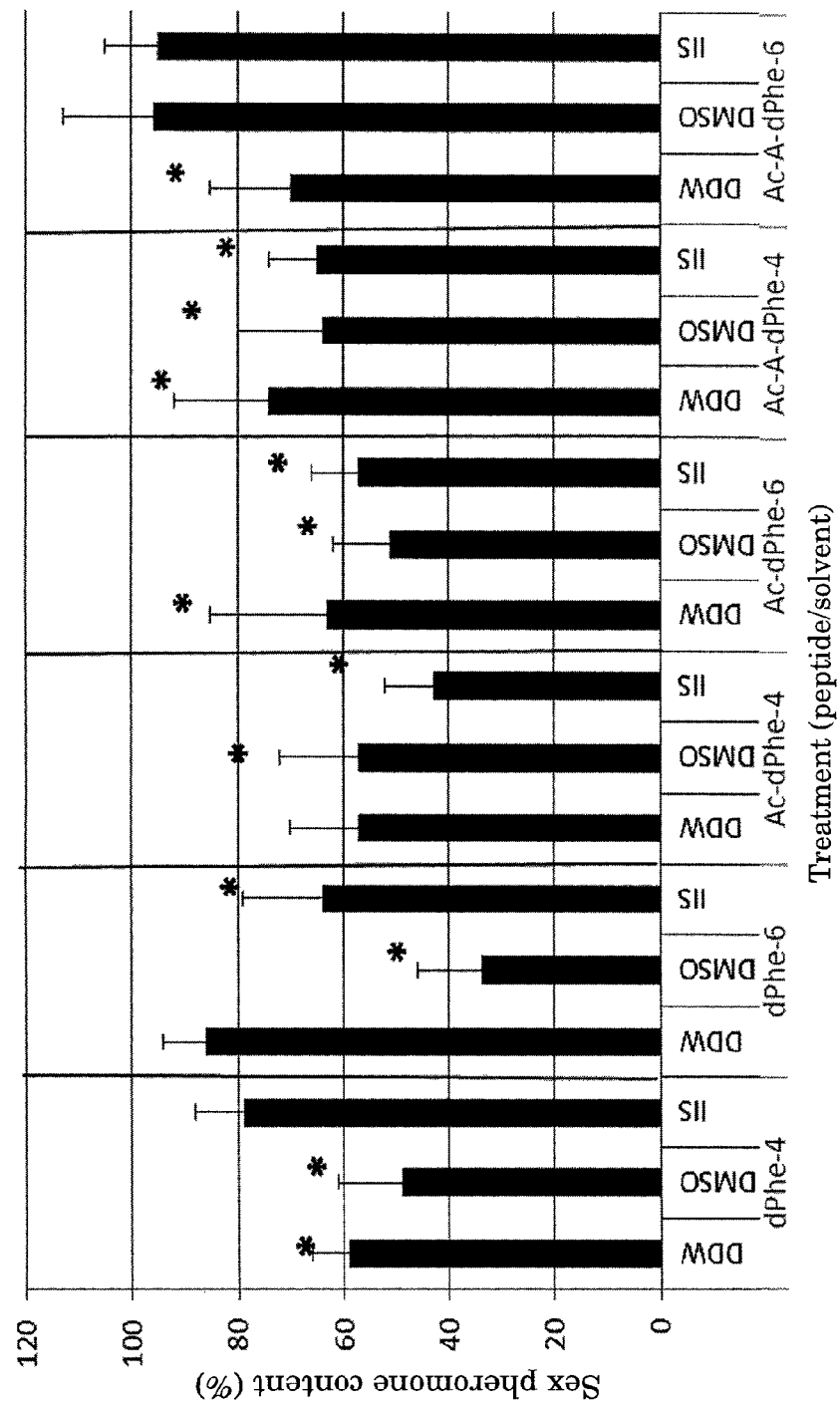

FIG. 5A to FIG. 5C are graphs showing the effect of topically applied peptides on inhibition of sex pheromone biosynthesis in *Heliothis peltigera* female moths.

The tested peptides are those listed in Table 1 (1-6, respectively). Peptides were tested at a concentration of 1000 pmol (5A), 300 pmol (5B) or 100 pmol (5C) and were applied in DDW, DMSO and IIS for 7h.

Sex pheromone content is expressed as a percentage of the endogenous pheromone content obtained using control untreated moths (defined as 100%). Statistical analysis compared pheromone content in the presence of each peptide in a given solvent (DDW, DMSO or ITS) with that obtained with the solvents themselves (indicated by an asterisk). There was no significant difference between the amount of pheromone content generated by untreated control females and that of the solvent treated moths.

Figure 6:
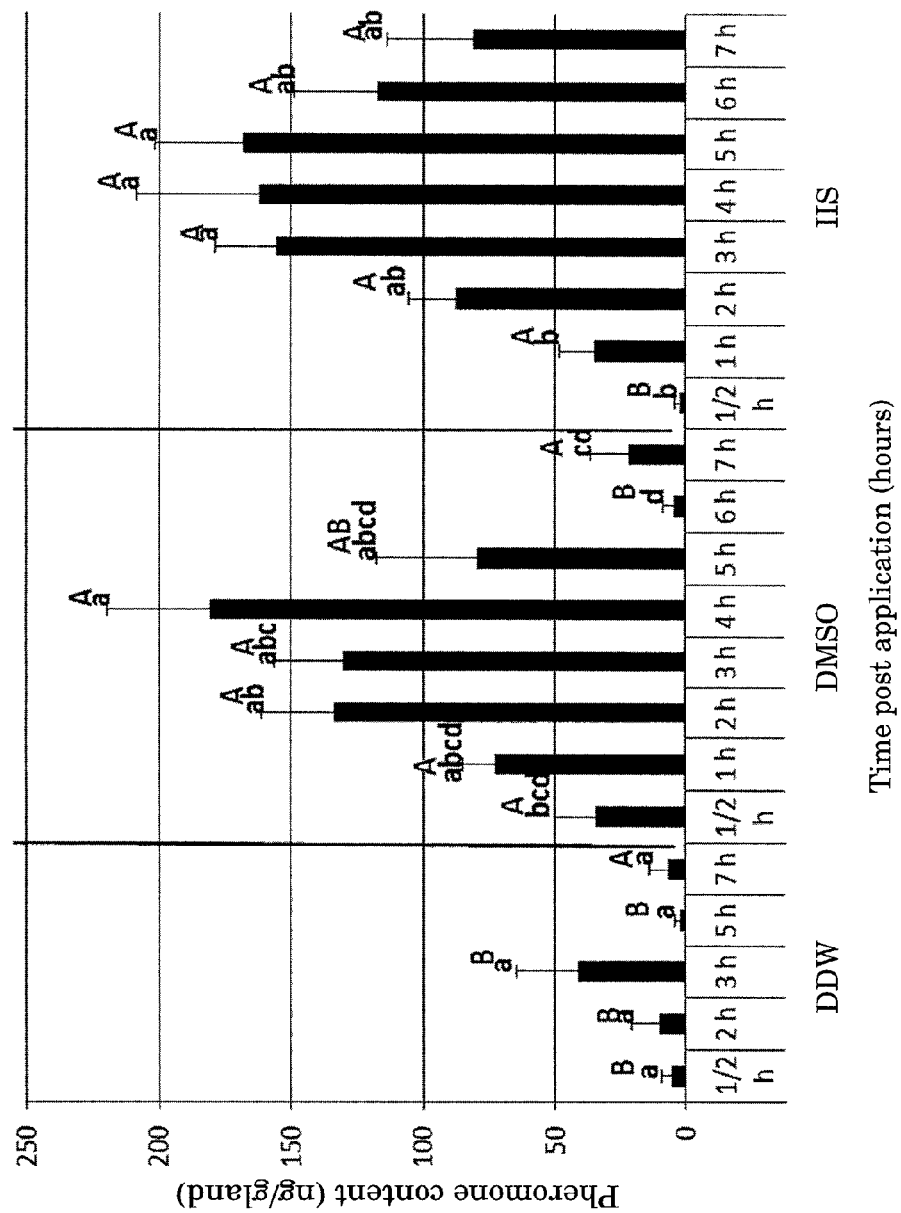

FIG. 6. is a graph showing the effect of a topically applied peptide (Peptide 12 in Table 1) on stimulation of sex pheromone biosynthesis in *Heliothis peltigera* female moths.

The peptide was tested at a concentration of 300 pmol and was applied in DDW, DMSO and IIS for different times (ranging from 0.5 to 7 h).

Statistical analysis compared pheromone content in the presence of the peptide in a given solvent (DDW, DMSO or IIS) at different time points (indicated by small black letters) and between solvents at the same time point (indicated by capital light grey letters). Bars with the same letter do not differ significantly.

Figure 7A:
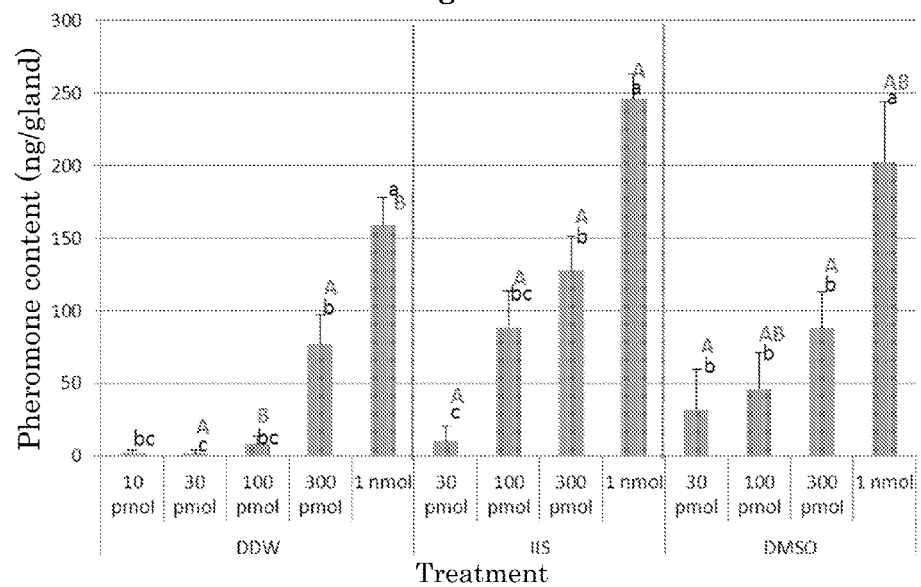
Figure 7B:
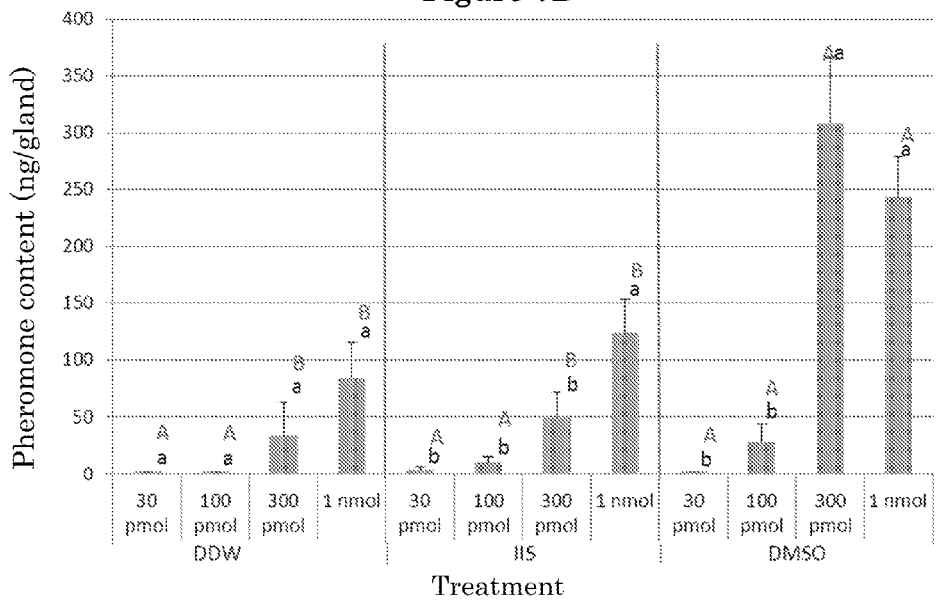

FIG. 7A and FIG. 7B are graphs showing the dose-response of a topically applied peptide [Peptide 12 (7A) and Peptide 11 (7B)] on stimulation of sex pheromone biosynthesis in *Heliothis peltigera* female moths. The peptide was tested at the indicated concentrations and was applied in DDW, IIS and DMSO for 3 h.

Statistical analysis compared pheromone content in the presence of the peptide in a given solvent (DDW, DMSO or IIS) at different concentrations (indicated by black letters) and between solvents at the same concentration (indicated by capital light grey letters). Bars with the same letter do not differ significantly.

Figure 8:
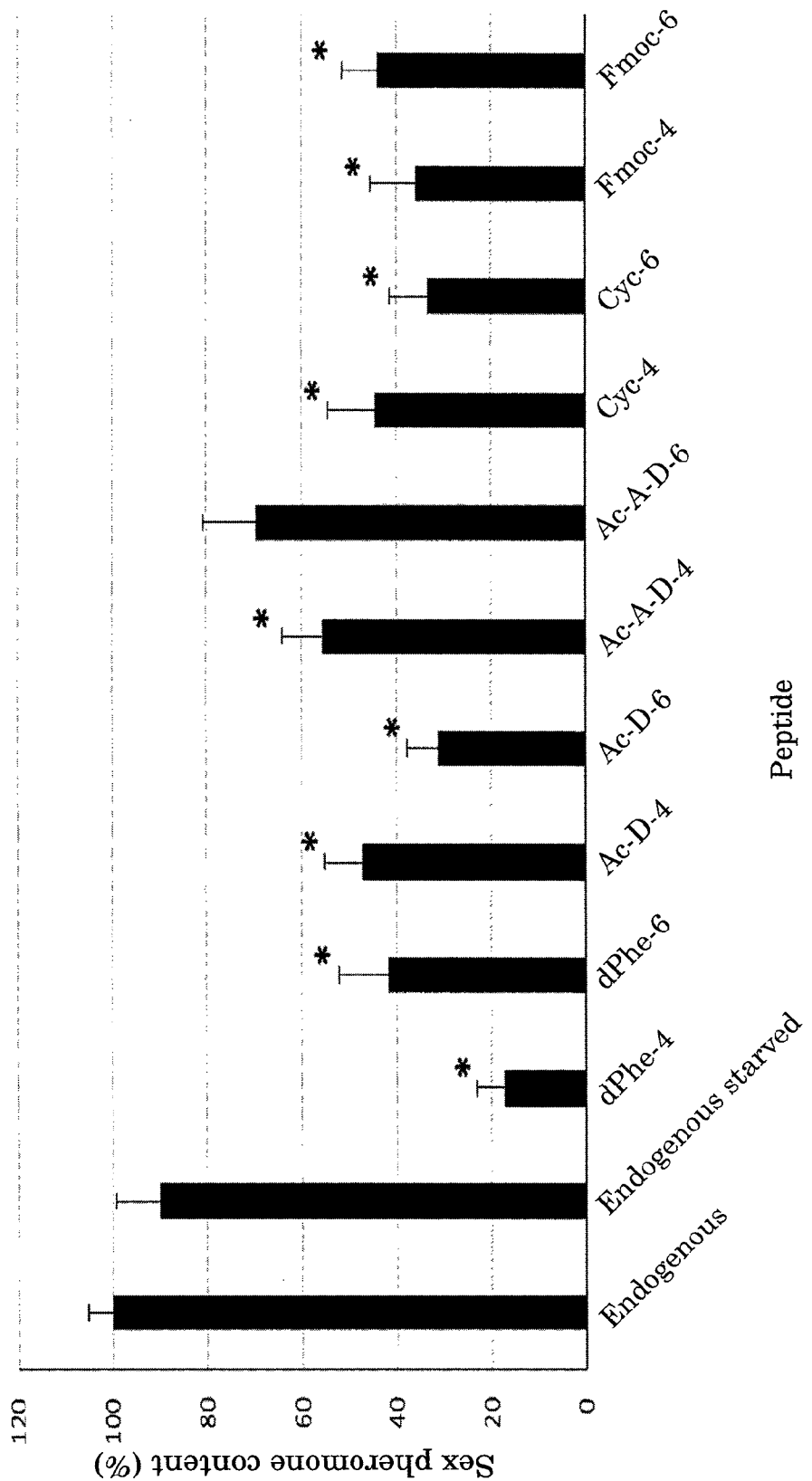

FIG. 8. is a graph showing the effect of orally ingested peptides on inhibition of sex pheromone biosynthesis in *Heliothis peltigera* female moths.

The peptide was tested at a concentration of 1000 pmol for 1h and was provided in 10% sugar solution made up in DDW.

Sex pheromone content is expressed as a percentage of the endogenous pheromone content obtained using control untreated moths (defined as 100%). Statistical analysis compared pheromone content in the presence of each peptide with that obtained with moth starved for the same amount of time prior to their exposure to a 10% sugar solution (indicated by an asterisk). There was no significant difference between the amount of pheromone content generated by untreated control females and that of starved moths.

Figure 9:
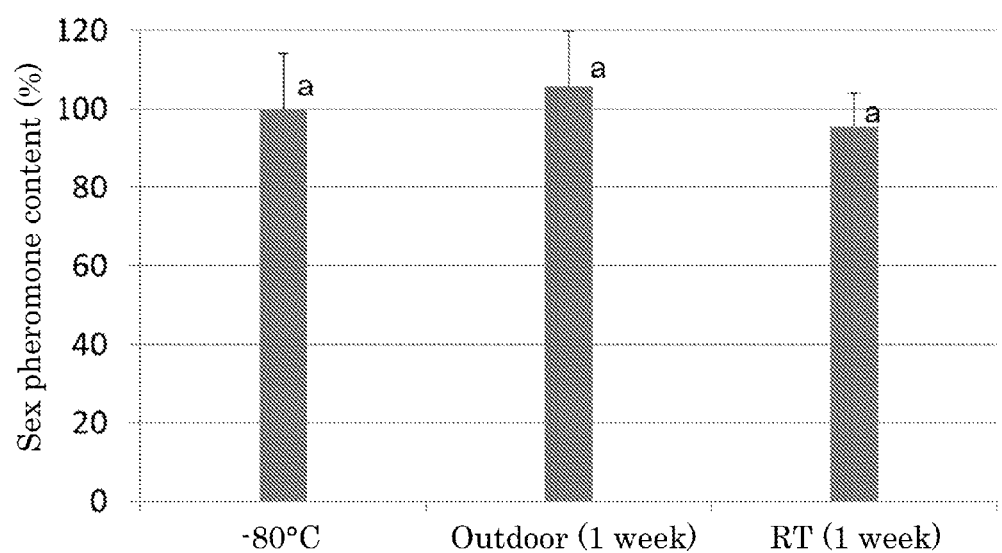

FIG. 9. is a graph showing the stability of Peptide 12 in a powder form under different storage conditions.

The stability was evaluated by determining sex pheromone production in *Heliothis peltigera* females exposed to said peptide.

The storage conditions are: (i) exposure to direct sunlight and an average temperature of about 31° C. for 1 week ("outdoor 1 week"); (ii) room temperature (RT); and (iii) −80° C.

Sex pheromone content is expressed as a percentage of the pheromone content obtained by injection of a peptide stored at −80° C. (defined as 100%). Statistical analysis compared pheromone content generated by injection of a peptide stored at room temperature (RT) for 1 week or a peptide kept for 1 week outdoors with that of the control (a peptide stored at −80° C.). There was no significant difference between the amount of pheromone content generated by the above treatments. Bars with the same letter do not differ significantly.

Figure 10A:
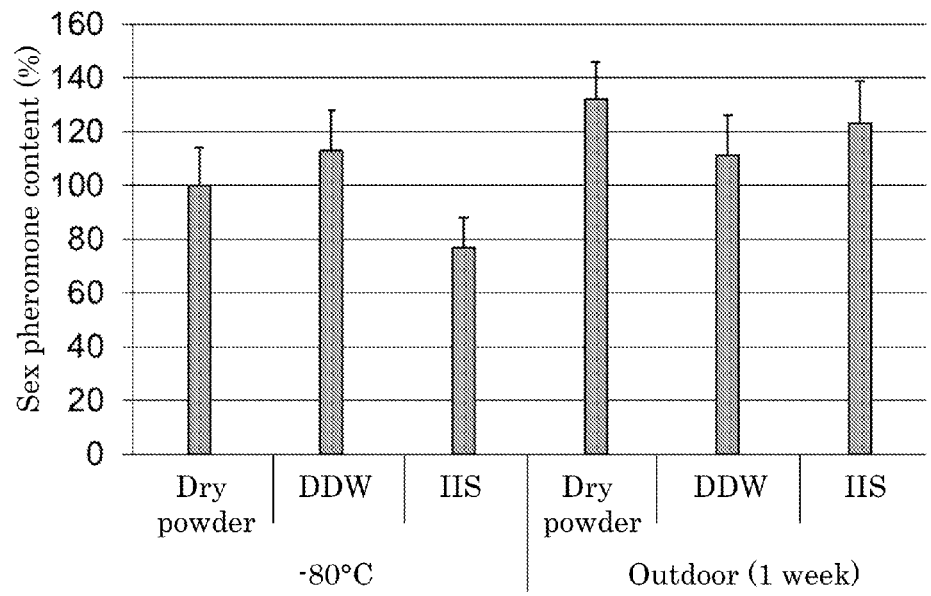
Figure 10B:
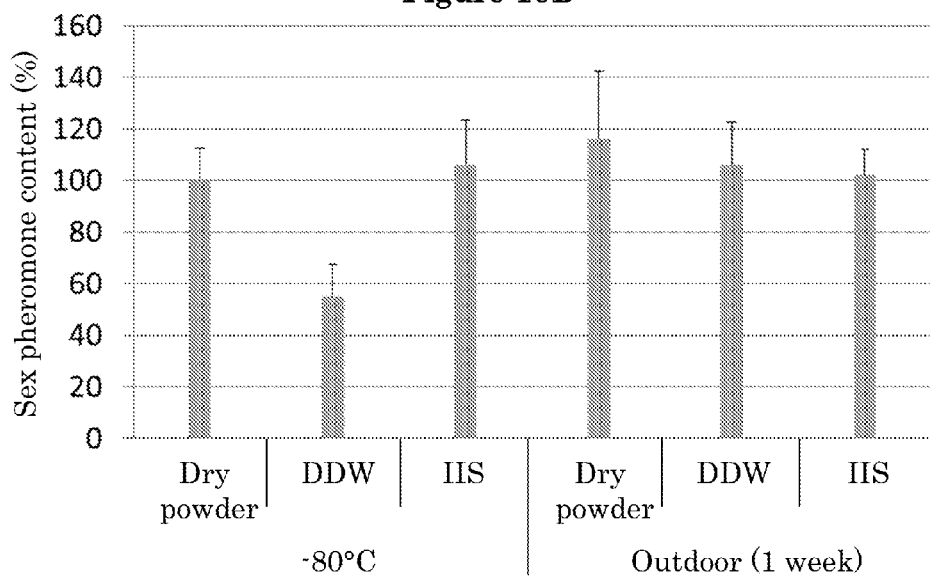

FIG. 10A and FIG. 10B are graphs showing the stability of Peptide 12 dissolved in DDW or ITS at a concentration of 1 nmol (10A) or 100 pmol (10B) under different storage conditions.

The stability was evaluated by determining sex pheromone production in *Heliothis peltigera* females exposed to said peptide.

The storage conditions are: (i) exposure to direct sunlight and an average temperature of about 31° C. for 1 week ("outdoor 1 week"); and (ii) −80° C.

Sex pheromone content is expressed as a percentage of the pheromone content obtained by injection of a peptide stored as a dry powder at −80° C. (defined as 100%). Statistical analysis compared the pheromone content generated by the different treatments with that of the control (a peptide stored at −80° C.). There was no significant difference between the amount of pheromone content generated by the above treatments.

Figure 11A:
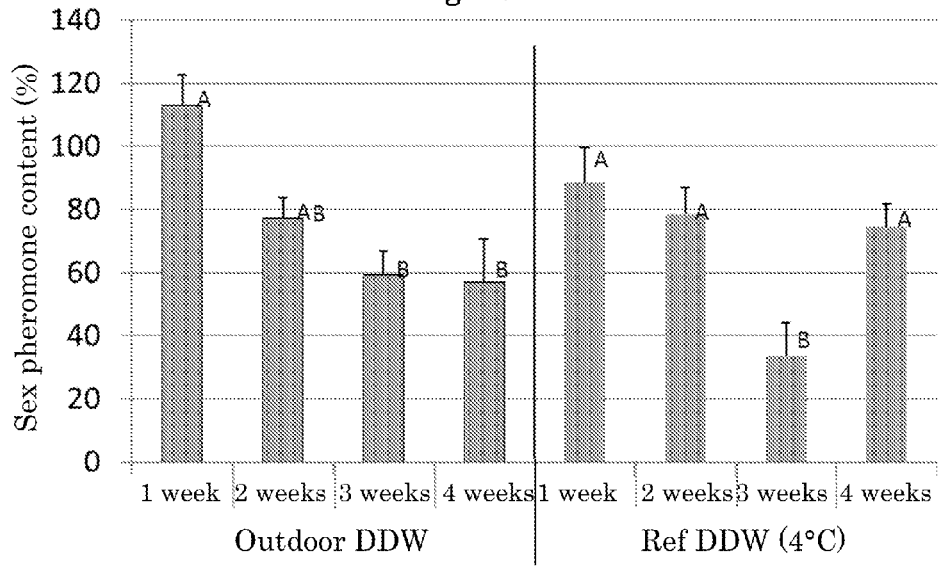
Figure 11B:
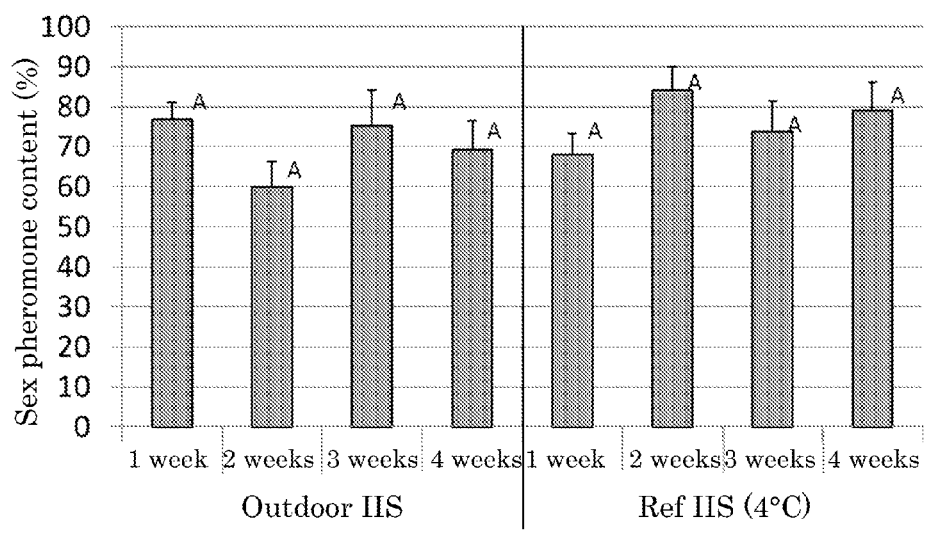

FIG. 11A and FIG. 11B are graphs showing the stability of Peptide 12 dissolved in DDW (A) or IIS (B) at a concentration of 1 nmol, and exposed to direct sunlight and temperatures in the range of 27° C. to 31° C. for 1-4 weeks or by a peptide stored at 4° C. for 1-4 weeks.

The stability was evaluated by determining sex pheromone production in *Heliothis peltigera* females exposed to said peptide.

Activity is expressed as a percentage of that obtained by Peptide 12 stored at −80° C. (defined as 100%, not shown in the figures).

Statistical analysis compared activity at the same storage time at 4° C. and outdoor, and as a function of time within the same treatment (outdoor or 4° C.) as a function of storage time (capital letters). No differences were indicated at the different storage times between peptides kept outdoor and at 4° C. Bars with the same letter do not differ significantly.

FIG. 12. is a graph showing the melanotropic inhibitory activity of the peptides of the invention against different stimulators of the PK/PBAN family: PBAN, PT (pheromonotropin), LPK (leucopyrokinin), DH (diapause hormone).

Degree of cuticular melanization is expressed as a percentage of the melanization obtained by injection the elicitor itself (PBAN, PT, LPK or DH) in the absence of the tested peptide (not shown). Statistical analysis compared the degree of melanization in the presence and absence of the tested peptide with any given elicitor. An asterisk indicates a significant difference between the degree of melanization obtained in the presence of the peptide.

DETAILED DESCRIPTION OF THE INVENTION

Activity studies of the different compounds were performed by examining their pheromonotropic and melanotropic inhibitory activity as well as their cuticular and oral bioavailability. Activity was tested mainly on *Heliothis peltigera* and *Spodoptera littoralis*, using bioassays as described in the Examples section below. The tested compounds are: Arg-Tyr-Phe-[dPhe]-Pro-Arg-Leu-amide (SEQ ID NO: 12); Arg-Tyr-Phe-Ser-Pro-[dPhe]-Leu-amide (SEQ ID NO: 13); Acetyl-Arg-Tyr-Phe-[dPhe]-Pro-Arg-Leu-amide (SEQ ID NO: 14); Acetyl-Arg-Tyr-Phe-Ser-Pro-[dPhe]-Leu-amide (SEQ ID NO: 15); Acetyl-Ala-[dPhe]-Pro-Arg-Leu-amide (SEQ ID NO: 16); Acetyl-Ala-Ser-Pro-[dPhe]-Leu-amide (SEQ ID NO: 17); Cyclohexyl-Ala-[dPhe]-Pro-Arg-Leu-amide (SEQ ID NO: 18); Cyclohexyl-Ala-Ser-Pro-[dPhe]-Leu-amide (SEQ ID NO: 19); Fmoc-Ala-[dPhe]-Pro-Arg-Leu-amide (SEQ ID NO: 20); Fmoc-Ala-Ser-Pro-[dPhe]-Leu-amide (SEQ ID NO: 21) (see Table 1). The agonistic peptides 11 and 12 (Tyr-Phe-Trp-Pro-Arg-Leu-amide (SEQ ID NO: 22); and Acetyl-Tyr-Phe-Trp-Pro-Arg-Leu-amide (SEQ ID NO: 23)) (see Table 1) were tested for bioavailability and environmental stability.

Fmoc is fluorenylmethyloxycarbonyl, Cyc is cyclohexyl, and Ac is acetyl.

The effect of the above peptides on various PK/PBAN activities was examined by using various assays at different concentrations, ranging from 1 pmol to 1000 pmol. Examples of such assays include:

a) Topical application (TA), to determine their cuticular penetrability;

b) Injection, to test their agonistic/antagonistic properties and to analyze their bio-stability;

c) Feeding, to examine their oral bioavailability; and d) Stability, to test their outdoor storage stability.

In vivo pheromonotropic bioassays in *Heliothis peltigera* female moths reviled that the peptides of the invention are pure antagonists, and have no agonistic activity (see FIGS. 1A and 1B): antagonistic activity was tested by topically applying the peptides of the invention dissolved in DDW (double distilled water) or IIS (0.5% ethanol, 0.05% Tween-80 in DDW) (see FIG. 2). As can be seen from FIG. 2, most of the tested peptides easily penetrate the cuticule of adult insects, and reach their target organ (i.e. the pheromone gland), wherein the most active peptide is Ac-A-dPhe-4 (dissolved in DDW), exhibiting 83% inhibition of pheromone biosynthesis.

Another phenomena observed is that the composition of the solution used has hardly any effect on the peptides bioactivity, as can be seen when comparing DDW- and IIS-dissolved peptides.

In an attempt to determine the effective dose that should be used, dose response analysis was performed. As can be seen from FIGS. 3A & 3B, the peptides of the invention are highly penetrable and bioactive even at a dose as low as 1 pmol. In addition, the peptides of the invention are stable and active for long periods of time, and have very high bio-stability within the insect for at least 7 hours after application (see FIGS. 4 and 5A-C).

Notably, it seems that the carrier solvent used to transfer the peptides of the invention to the insects (by topical application) has almost no effect on cuticle penetration. Without wishing to be bound by any particular theory, the inventors believe that this is probably due to the fact that all the peptides of the invention contain a dPhe residue which may have a role in bioavailability greater than that of the carrier solvent.

Accordingly, the peptides of the invention are highly bio-stable in vivo and are capable of penetrating the insect's cuticle very quickly (within one hour) (see FIGS. 2-4). As used herein, the term "highly bio-stable" means that the peptides maintain their biological activity for at least 7 hours after penetration into the insect. In addition, the results show that the peptides of the invention are pure antagonists

TABLE 1

| | Name | Formula | Amino acids (from N- to C-terminus) | SEQ ID NO: |
|---|---|---|---|---|
| 1 | dPhe-4 | RYF[dF]PRLa | Arg-Tyr-Phe-[dPhe]-Pro-Arg-Leu-amide | 12 |
| 2 | dPhe-6 | RYFSP[dF]La | Arg-Tyr-Phe-Ser-Pro-[dPhe]-Leu-amide | 13 |
| 3 | Ac-dPhe-4 | Ac-RYF[dF]PRLa | Acetyl-Arg-Tyr-Phe-[dPhe]-Pro-Arg-Leu-amide | 14 |
| 4 | Ac-dPhe-6 | Ac-RYFSP[dF]La | Acetyl-Arg-Tyr-Phe-Ser-Pro-[dPhe]-Leu-amide | 15 |
| 5 | Ac-A-dPhe-4 | Ac-A[dF]PRLa | Acetyl-Ala-[dPhe]-Pro-Arg-Leu-amide | 16 |
| 6 | Ac-A-dPhe-6 | Ac-ASP[dF]La | Acetyl-Ala-Ser-Pro-[dPhe]-Leu-amide | 17 |
| 7 | Cyc-A-dPhe-4 | Cyc-A[dF]PRLa | Cyclohexyl-Ala-[dPhe]-Pro-Arg-Leu-amide | 18 |
| 8 | Cyc-A-dPhe-6 | Cyc-ASP[dF]La | Cyclohexyl-Ala-Ser-Pro-[dPhe]-Leu-amide | 19 |
| 9 | Fmoc-A-dPhe-4 | Fmoc-A[dF]PRLa | Fmoc-Ala-[dPhe]-Pro-Arg-Leu-amide | 20 |
| 10 | Fmoc-A-dPhe-6 | Fmoc-ASP[dF]La | Fmoc-Ala-Ser-Pro-[dPhe]-Leu-amide | 21 |
| 11 | Peptide 11 | YFWPRLa | Tyr-Phe-Trp-Pro-Arg-Leu-amide | 22 |
| 12 | Peptide 12 | Ac-YFWPRLa | Acetyl-Tyr-Phe-Trp-Pro-Arg-Leu-amide | 23 | capable of inhibiting PK/PBAN activities (e.g. sex pheromone biosynthesis or cuticular melanin synthesis) in the insect over 90%, even at a dose of 1 pmol. (FIG. 3A).

As can be seen in FIGS. 6 & 7, the solvent carrier used to topically apply the peptide, affects significantly the peptide's penetrability. However, the presence of a dPhe residue in the peptide improves the peptide's penetrability and over-rules the effect of the carrier. Accordingly, one aspect of the invention is peptide fragments and analogs derived from the amino acid sequence of PK/PBAN, having at least one dPhe residue. Another aspect is insecticides comprising said peptides, and use thereof to treat and/or prevent insect infestations.

Oral bioavailability tests (see FIG. 8) show that the peptides of the invention have high inhibitory activity, namely over 60% inhibition. This means that the presence of a dPhe residue in the peptide might also improves its oral bioavailability and stability. Accordingly, an aspect of the invention is peptide fragments and analogs derived from the amino acid sequence of PK/PBAN, having at least one dPhe residue, with improved cuticle penetrability and/or oral bioavailability.

Environmental stability tests show that PK/PBAN derived short peptides are highly stable. As used herein in, the term "highly stable" means that the peptides do not lose their activity after prolong storage, either as a dry powder or dissolved in a solvent. As used herein the term "prolong storage" means storage for several years at room temp without losing activity. Moreover, the PK/PBAN derived short peptides are resistant to direct sunlight and are highly stable at a temperature range of from −80° C. to 31° C. According to one specific embodiment, the peptides are highly stable for even more prolonged period of time when dissolved in IIS (see FIGS. 9-11)

The peptides of the present invention are thus useful insecticides as they are potent PK/PBAN activities inhibitors, including pheromone biosynthesis and melanin formation.

Unlike other peptides known in the art, the peptides of the present invention are highly efficient insecticides as they are (i) effective even at low doses of less than 1 pmol, (ii) pure antagonists, (iii) highly bioavailable through the cuticle and/or orally, and (iv) extremely stable, both during storage and after intake by the insects. The peptides of the present invention have been formulated to minimize harmful side-effects to animals and humans, first by being highly specific to insects, and second by being effective at extremely low doses which could not affect a large animal. Accordingly, in one embodiment, the peptides of the invention can also be applied in environmentally safe carriers, e.g. DDW and IIS.

The peptides of the present invention may be applied to the insects by any known mean, for example by spraying, fumigation, rubbing, feeding, watering, etc. For ease of application, the peptides of the invention may be dissolved in any aqueous (water) solution, such as DDW, IIS, etc.

Those skilled in the art will readily understand that the peptides of the invention can be used either as a single insect control agent or can be used in any combination thereof in the preparation of insect control compositions. Notably, the peptides of the invention can be used to inhibit additional functions mediated by PK/PBAN peptides and be applied to various insect pests. In addition, the skilled artisan would understand that the characteristics of the peptides of the invention achieved by their various modifications, e.g. their metabolically and environmentally stability, their oral bioavailability, and their capability to penetrate through the cuticle, can be utilized in the preparation of additional insect control peptides based on other insect neuropeptides or peptides.

The following examples are set forth to further illustrate the present invention. The below examples, however, should not be construed in any way as limiting the present invention in any manner. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Bioassays a) Topical Application (TA)
This assay is used to determine cuticular penetrability.
The tested peptides are applied onto the insect (e.g. moths) at scotophase (when pheromone is naturally synthesized) in a given solvent for the indicated times.
b) Injection
This assay is used to test the agonistic properties of the tested peptides (in adult females), and to determine the peptides melanotropic agonistic or antagonistic properties (in larvae). It was also used to determine the activity of peptides that were stored outdoors for different amounts of time.
The peptides are injected into either adult female insects (e.g. moths) at photophase (when pheromone is not synthesized naturally, but the insect has the ability to produce pheromone upon stimulation with a agonist) or into $5^{th}$ instar larvae.
Agonistic properties were tested by injection of the peptides alone; antagonistic properties were determined by injection of the peptide together with a stimulator.
Pheromone content was determined 2 h post injection.
c) Feeding
This assay is used to determine oral bioavailability of the peptides.
Adult females were exposed to the peptides of the invention dissolved in a 10% sugar solution.

Example 2

Lack of Agonistic Activity

Figure 1A:
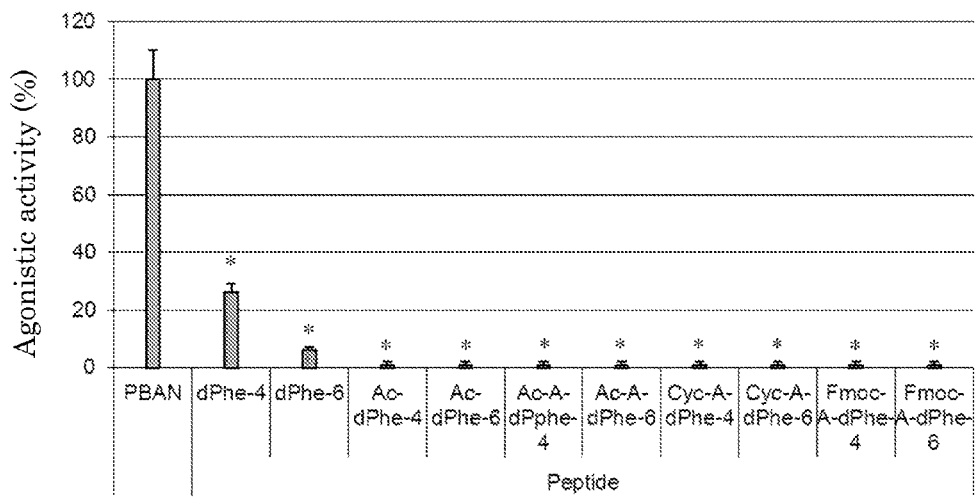
FIG. 1A and FIG. 1B are graphs showing the pheromonotropic agonistic activity of the peptides at a concentration of 100 pmol (1A) and 1 nmol (1B).
Figure 1B:
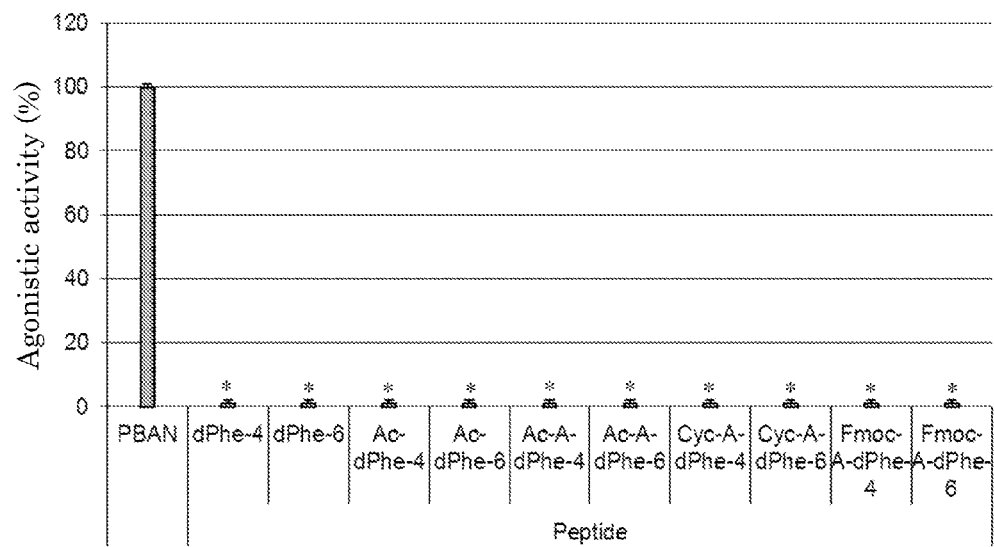

Peptides 1-10 have been found to be pure antagonists, meaning they lack any agonistic activity. This was determined by an in vivo pheromonotropic bioassay in *Heliothis peltigera* female moths: peptides were injected to the females and pheromone production was monitored quantitatively by gas chromatography.
The inactivity of all peptides at 100 pmol and 1 nmol is depicted FIGS. 1A & 1B.

Example 3

Cuticular Bioavailability

Antagonistic activity was tested at a concentration of 10 pmol and the peptides were topically applied in two solvents: DDW and IIS (FIG. 2). Under the tested conditions (where the peptides were applied one hour prior to pheromone analysis) most peptides exhibited a high cuticular penetrability and bioactivity as indicated by a significant inhibition of pheromone production compared to the carrier solvent itself. Three peptides: dPhe-4 and Cyc-A-dPhe-4 in IIS and dPhe-6 in DDW failed to lower pheromone content compared to the solvent, probably due to poor cuticular penetrability. The most active peptide was Ac-A-dPhe-4 in DDW which inhibited pheromone biosynthesis by 83%. Ac-A-dPhe-6 was the second best in IIS inhibiting pheromone biosynthesis by 74%. Comparison of the activity of each peptide in DDW and IIS did not reveal significant differences between the solvents under the tested conditions. Similar results were obtained when some of the peptides (Ac-A-dPhe-4, Ac-A-dPhe-6, Cyc-A-dPhe-4 and Fmoc-A-dPhe-4) were tested in tap water: No differences were obtained between peptides applied in IIS vs. tap water.

Example 4

Dose Response

The dose response of the two most active peptides, namely Ac-A-dPhe-4 and Ac-A-dPhe-6, at a concentration range of 1 to 1000 pmol (FIGS. 3A & 3B) have been analyzed. Both peptides have been found to be highly active: they easily penetrated through the cuticle (when dissolved in DDW) and inhibited pheromone production by 80-99%, at all tested concentrations. Only minor differences in activity is observed as a function of a dose (with the exception of Ac-A-dPhe-4 at 1000 pmol, which inhibited pheromone production to a lesser extent of about 50%).

Importantly, these results show the high penetrability and bioactivity of both peptides at the very low concentration of 1 pmol.

All experiments were carried out at the scotophase and the peptides were applied one hour before pheromone glands were excised (+5) and tested for pheromone content (at the $6^{th}$ hour of the scotophase when the pheromone content is at its highest level). The high inhibition obtained under the tested conditions, indicates the extremely fast and high penetrability and bioactivity of the peptides of the invention.

In order to test whether the peptides are active for longer periods of time, they were applied (at a dose of 1 nmol) 3 and 7 hours prior to pheromone analysis, (indicated in FIG. 4 by +3 and −1, respectively). Ac-A-dPhe-4 and Ac-A-dPhe-6 were applied in DDW one hour before the onset of scotophase and at the $3^{rd}$ and $5^{th}$ hour of scotophase. The data in FIG. 4 clearly reveal that the peptides are active for at least 7 hours as indicated by the significantly lower amount of pheromone in the gland at the time point of −1. The amount of pheromone in female moths treated at the $3^{rd}$ hour of scotophase was lower than that found in females treated for 7 hours, and that of females treated for just 1 hour was the lowest, although a comparison between the activity of each peptide at the three time points indicated that the potency of Ac-A-dPhe-6 did not differ as a function of application time.

Example 5

Cuticle Penetration

Based on the above results, the ability of the peptides to penetrate the cuticle and inhibit sex pheromone biosynthesis when applied 7 h prior to pheromone analysis, was tested at concentration of 1 nmol, 300 pmol and 100 pmol.

The data in FIGS. 5A-C show that the tested peptides are active at all 3 concentrations in all solvents (DDW, DMSO and IIS). Comparison of the activity of each peptide as a function of carrier used for topical application revealed no differences between the peptides at all three concentrations (except for dPhe-4, which had a lower activity in DDW and IIS compared to DMSO at 300 pmol).

The lack of differences in activity as a function of carrier solvents may result from the fact that all peptides contain a dPhe residue which may have a role in bioavailability that over-rules the importance of the carrier solvent. Comparison of the activity of each peptide as a function of the dose in the different solvents did not reveal any differences in activity in any of the solvents (except for Ac-A-dPhe-4 which was less active at 100 pmol compared to 300 and 1000 pmol in IIS and DMSO). This lack of differences between concentrations indicates that even the lowest dose used in this series of experiments (i.e. 100 pmol) was still very high compared to the dose needed for inhibition and thus, did not enable to obtain a real dose response. This is further strengthen by the results in FIGS. 3A & 3B which indicate high inhibitory activity at low doses of the peptides (although the former experiments were carried out only for 1 h).

Example 6

Solvent Effect on Penetrability

Examination of the effect of carrier solvent on penetrability and activity was tested as a function of time and concentration with peptides 11 and 12 (see Table 1) which are agonistic peptides, i.e. stimulate sex pheromone production in female moths. FIG. 6 clearly indicates that the carrier used affect the bioavailability of the peptide. For instance, IIS has been found to be the best carrier: both the activity amplitude and the duration at which the peptide was still active, are the highest and longest with IIS as the carrier.

Dose response analysis of Peptide 12 (in Table 1) also showed a higher activity in IIS compared to DDW or DMSO (FIG. 7A). However, peptide 11 (in Table 1) had barely any activity in DDW and IIS, but was very active in DMSO (FIG. 7B). These results indicate the importance of the solvent on penetrability in peptides lacking a dPhe residue.

Example 7

Oral Bioavailability

The ability of the antagonistic peptides to inhibit sex pheromone biosynthesis after oral ingestion was tested with all peptides. FIG. 8 shows that high inhibitory activity (over 60% inhibition) in sex pheromone production by peptides dPhe-4, Ac-dPhe-6, Cyc-A-dPhe-6 and Fmoc-A-dPhe-4. All other peptides (except Ac-A-dPhe-6) exhibited a lower but significant activity (between 40 and 55%).

Example 8

Environmental Stability

In order to evaluate the environmental stability of the peptides, peptide 12 (in Table 1) was tested. Stability was monitored by exposing a tube containing the peptide, either in the form of a dry powder or in solution made up in either DDW or IIS at a concentration of 100 pmol or 1 nmol, to direct sun light and a temperature range of 27 to 31° C. ("outdoor").

Exposure of the peptide (in a form of a powder) to direct sunlight and an average temperature of 31° C. for 1 week revealed that its ability to stimulate sex pheromone production in *Heliothis peltigera* female moths does not differ significantly from that of a peptide stored either at room temperature (RT) or −80° C. (FIG. 9) indicating that the peptide is very stable under the tested conditions.

Exposure for 1 week in direct sunlight and an average temperature of 31° C. of the peptide in DDW or IIS (at a concentration of 1 nmol) revealed no significant differences between the peptide activity, even when compared with the dry powder peptide. Moreover, no significant difference was observed in the activity of the "outdoor" peptide and a peptide stored at −80° C., meaning the peptide is not affected by exposure to sunlight or high temperature either in a dry or dissolved state (FIG. 10A). Similar results were obtained at a lower dose of the peptide, of 100 pmol (FIG. 10B).

The peptide was also tested for stability for 4 weeks when dissolved in either DDW or IIS, at a concentration of 1 nmol, under the same conditions as above at a temperature range of 27° C. to 31° C. The results in FIGS. 11A & 11B show that there is a stability difference between the two solvents: in DDW the activity dropped in the course of storage although there were no significant differences between the outdoor and the 4° C. stored samples; and in IIS the peptide was much more stable in the course of the outdoor storage. All samples exhibited a similar activity and the outdoor samples induced sex pheromone production to an extent similar to that obtained by samples stored at 4° C.

The exposure of the peptides to outdoor conditions (i.e., direct sun light and a temperature of about 27° C. to about 31° C.) either as a dry powder or dissolved in a solution at dose of 100 pmol or 1 nmol, does not result in activity loss. Nevertheless, it seems that the peptide is more stable when dissolved in IIS than in DDW when exposed to outdoor conditions for prolonged period of time (i.e., 4 weeks).

Example 9

Inhibition of Melanin Formation: Moth Larvae

The ability of the peptides to inhibit cuticular melanin synthesis was tested in *Spodoptera littoralis* larvae.

Inhibitory activity was tested by injecting the peptides to *Spodoptera littoralis* larvae together with a given stimulator: PBAN, PT, LPK and DH. Inhibition is expressed as 100 minus the ratio in percentage (%) between the extents of cuticular melanization obtain in the presence and absence of the tested peptide (Table 2).

Figure 12:
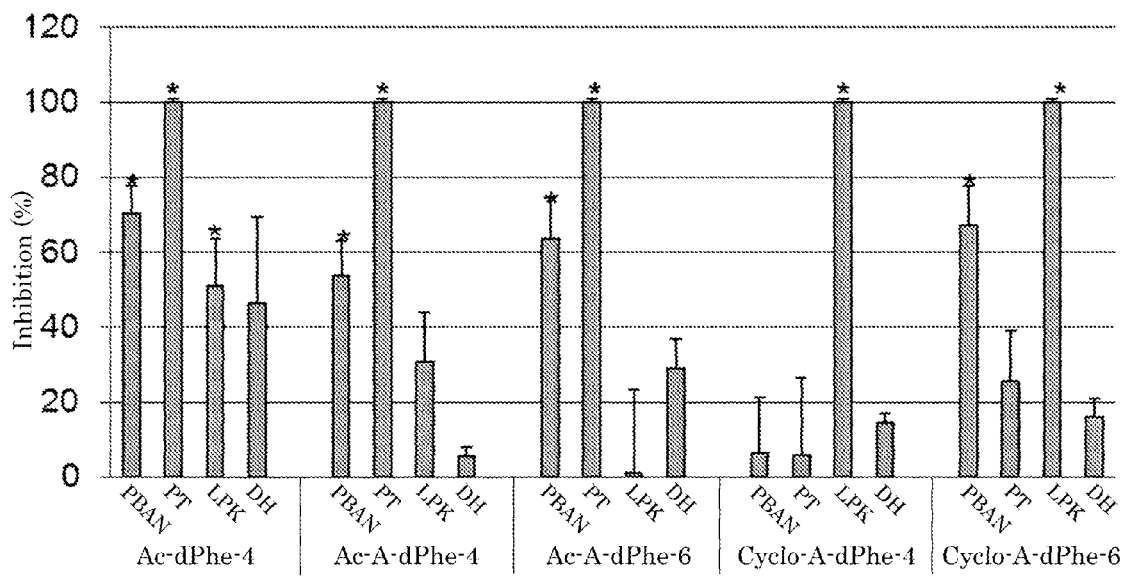

Interestingly, the tested peptides were selective against different melanin synthesis stimulators, namely, none of the peptides inhibited all stimulators: 4 inhibited PBAN (Ac-dPhe-4, Ac-A-dPhe-4, Ac-A-dPhe-6, and Cyclo-A-dPhe-6); 3 inhibited PT (Ac-dPhe-4, Ac-A-dPhe-4, Ac-A-dPhe-6); 4 inhibited LPK (Ac-A-dPhe-4, Ac-A-dPhe-6, Cyclo-A-dPhe-4 and Cyclo-A-dPhe-6) and none inhibited DH. (FIG. 12 and Table 2).

The results demonstrate that the peptides of the invention are not only useful as pheromone biosynthesis inhibitors, but some are also potent pure antagonists capable of inhibiting melanin formation evoked by different stimulators of the PK/PBAN family of peptides.

TABLE 2

Melanotropic inhibitory activity of peptides

| | Stimulator | | | |
|---|---|---|---|---|
| | PBAN 100 pm | PT 100 pm | LPK 100 pm | DH 100 pm |
| dPhe-4 | 18 | 59 | 10 | 33 |
| dPhe-6 | 49 | *74* | *78* | 15 |
| Ac-dPhe-4 | 70 | *100* | 51 | 22 |
| Ac-dPhe-6 | *59* | 100 | 8 | 35 |
| Ac-A-dPhe-4 | 54 | *100* | 31 | 6 |
| Ac-A-dPhe-6 | *63* | *100* | 0 | 29 |
| Cyc-A-dPhe-4 | 7 | 6 | *100* | 15 |
| Cyc-A-dPhe-6 | 67 | 26 | *100* | 15 |
| Fmoc-A-dPhe-4 | *68* | 100 | 100 | 28 |
| Fmoc-A-dPhe-6 | *67* | 100 | 100 | 35 |

Inhibition and experimental details are as indicated in FIG. 12 and Table 2 above. Italicized values indicate activity of pure antagonists; underlined values indicate inhibitory activity of peptides which are mixed agonists/antagonists (i.e., show some agonistic/stimulatory activity).

All methods described herein can be performed in any suitable order unless otherwise indicated herein or otherwise clearly contradicted by context. The use of any and all examples, or exemplary language (e.g., "such as") provided herein, is intended merely to better illustrate the invention and does not pose a limitation on the scope of the invention unless otherwise claimed. No language in the specification should be construed as indicating any non-claimed element as essential to the practice of the invention.

While the present invention has been described above in connection with the certain illustrative embodiments, it is to be understood that other similar embodiments may be used or modifications and additions may be made to the described embodiments for performing the same function of the present invention without deviating therefrom. Furthermore, all embodiments disclosed are not necessarily in the alternative, as various embodiments of the invention may be combined to provide the desired characteristics. Variations can be made by one having ordinary skill in the art without departing from the spirit and scope of the invention. Therefore, the present invention should not be limited to any single illustrative embodiment, but rather construed in breadth and scope in accordance with the recitation of the attached claims.

The invention claimed is:

1. A peptide fragment derived from the amino acid sequence of pyrokinin/pheromone biosynthesis activating neuropeptide (PK/PBAN) having the formula:

X-Ala-Y-Leu-amide (SEQ ID NO: 3), wherein X is Acetyl, Fmoc, or Cyclohexyl, and Y is Ser-Pro-[dPhe].

2. The peptide fragment of claim 1 which is selected from the group consisting of: Acetyl-Ala-Ser-Pro-[dPhe]-Leu-amide (SEQ ID NO: 7); Cyclohexyl-Ala-Ser-Pro-[dPhe]-Leu-amide (SEQ ID NO: 9); and Fmoc-Ala-Ser-Pro-[dPhe]-Leu-amide (SEQ ID NO: 11).

3. The peptide fragment of claim 1, wherein said peptide fragment has improved cuticle penetrability or oral bioavailability.

4. The peptide fragment of claim 3, wherein said peptide fragment is orally bioavailable.

5. A method for controlling insect infestation comprising dispersing the peptide fragment derived from the amino acid sequence of pyrokinin/pheromone biosynthesis activating neuropeptide (PK/PBAN) of claim 1 and an agricultural acceptable carrier onto a desired area.

6. A method for controlling insect infestation comprising administering the peptide fragment derived from the amino acid sequence of pyrokinin/pheromone biosynthesis activating neuropeptide (PK/PBAN) of claim 1 to the insects by feeding.

* * * * *

SEQUENCE LISTING

```
<160> NUMBER OF SEQ ID NOS: 23

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amide
```

```
<400> SEQUENCE: 1

Phe Ser Pro Arg Leu
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl, Fmoc or Cyclohexyl
<220> FEATURE:
<221> NAME/KEY: MOD_RES
<222> LOCATION: (4)..(4)
<223> OTHER INFORMATION: D-Phe or Ser
<220> FEATURE:
<221> NAME/KEY: MISC_FEATURE
<222> LOCATION: (4)..(6)
<223> OTHER INFORMATION: This region may encompass "D-Phe-Pro-Arg" or
      "Ser-Pro-D-Phe"
<220> FEATURE:
<221> NAME/KEY: MOD_RES
<222> LOCATION: (6)..(6)
<223> OTHER INFORMATION: Arg or D-Phe
<220> FEATURE:
<223> OTHER INFORMATION: C-term amide

<400> SEQUENCE: 2

Arg Tyr Phe Xaa Pro Xaa Leu
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl, Fmoc or Cyclohexyl
<220> FEATURE:
<221> NAME/KEY: MOD_RES
<222> LOCATION: (2)..(2)
<223> OTHER INFORMATION: D-Phe or Ser
<220> FEATURE:
<221> NAME/KEY: MISC_FEATURE
<222> LOCATION: (2)..(4)
<223> OTHER INFORMATION: This region may encompass "D-Phe-Pro-Arg" or
      "Ser-Pro-D-Phe"
<220> FEATURE:
<221> NAME/KEY: MOD_RES
<222> LOCATION: (4)..(4)
<223> OTHER INFORMATION: Arg or D-Phe
<220> FEATURE:
<223> OTHER INFORMATION: C-term amide

<400> SEQUENCE: 3

Ala Xaa Pro Xaa Leu
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
```

```
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term amide

<400> SEQUENCE: 4

Arg Tyr Phe Phe Pro Arg Leu
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (6)..(6)
<223> OTHER INFORMATION: D-Phe
<220> FEATURE:
<223> OTHER INFORMATION: C-term amide

<400> SEQUENCE: 5

Arg Tyr Phe Ser Pro Phe Leu
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (2)..(2)
<223> OTHER INFORMATION: D-Phe
<220> FEATURE:
<223> OTHER INFORMATION: C-term amide

<400> SEQUENCE: 6

Ala Phe Pro Arg Leu
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term amide

<400> SEQUENCE: 7

Ala Ser Pro Phe Leu
1               5
```

```
<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cyclohexyl
<220> FEATURE:
<221> NAME/KEY: MOD_RES
<222> LOCATION: (2)..(2)
<223> OTHER INFORMATION: D-Phe
<220> FEATURE:
<223> OTHER INFORMATION: C-term amide

<400> SEQUENCE: 8

Ala Phe Pro Arg Leu
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cyclohexyl
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term amide

<400> SEQUENCE: 9

Ala Ser Pro Phe Leu
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (2)..(2)
<223> OTHER INFORMATION: D-Phe
<220> FEATURE:
<223> OTHER INFORMATION: C-term amide

<400> SEQUENCE: 10

Ala Phe Pro Arg Leu
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (4)..(4)
<223> OTHER INFORMATION: D-Phe
```

```
<220> FEATURE:
<223> OTHER INFORMATION: C-term amide

<400> SEQUENCE: 11

Ala Ser Pro Phe Leu
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term amide

<400> SEQUENCE: 12

Arg Tyr Phe Phe Pro Arg Leu
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Phe
<220> FEATURE:
<223> OTHER INFORMATION: C-term amide

<400> SEQUENCE: 13

Arg Tyr Phe Ser Pro Phe Leu
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term amide

<400> SEQUENCE: 14

Arg Tyr Phe Phe Pro Arg Leu
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Acetyl
<220> FEATURE:
<221> NAME/KEY: MOD_RES
<222> LOCATION: (6)..(6)
<223> OTHER INFORMATION: D-Phe
<220> FEATURE:
<223> OTHER INFORMATION: C-term amide

<400> SEQUENCE: 15

Arg Tyr Phe Ser Pro Phe Leu
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (2)..(2)
<223> OTHER INFORMATION: D-Phe
<220> FEATURE:
<223> OTHER INFORMATION: C-term amide

<400> SEQUENCE: 16

Ala Phe Pro Arg Leu
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term amide

<400> SEQUENCE: 17

Ala Ser Pro Phe Leu
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cyclohexyl
<220> FEATURE:
<221> NAME/KEY: MOD_RES
<222> LOCATION: (2)..(2)
<223> OTHER INFORMATION: D-Phe
<220> FEATURE:
<223> OTHER INFORMATION: C-term amide

<400> SEQUENCE: 18

Ala Phe Pro Arg Leu
1               5
```

-continued

```
<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cyclohexyl
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term amide

<400> SEQUENCE: 19

Ala Ser Pro Phe Leu
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (2)..(2)
<223> OTHER INFORMATION: D-Phe
<220> FEATURE:
<223> OTHER INFORMATION: C-term amide

<400> SEQUENCE: 20

Ala Phe Pro Arg Leu
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term amide

<400> SEQUENCE: 21

Ala Ser Pro Phe Leu
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amide
```

```
<400> SEQUENCE: 22

Tyr Phe Trp Pro Arg Leu
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<223> OTHER INFORMATION: C-term amide

<400> SEQUENCE: 23

Tyr Phe Trp Pro Arg Leu
1               5
```